United States Patent [19]

Ouellette et al.

[11] Patent Number: 4,637,819
[45] Date of Patent: Jan. 20, 1987

[54] MACROSCOPICALLY EXPANDED THREE-DIMENSIONAL POLYMERIC WEB FOR TRANSMITTING BOTH DYNAMICALLY DEPOSITED AND STATICALLY CONTACTED FLUIDS FROM ONE SURFACE TO THE OTHER

[75] Inventors: William R. Ouellette; Daniel S. Alcombright; John J. Curro; E. Kelly Linman, all of Cincinnati, Ohio

[73] Assignee: The Procter & Gamble Company, Cincinnati, Ohio

[21] Appl. No.: 740,083

[22] Filed: May 31, 1985

[51] Int. Cl.⁴ .............................................. A61F 13/16
[52] U.S. Cl. .................................... 604/369; 604/378; 428/131
[58] Field of Search ................... 604/383, 384, 385 R, 604/380, 379, 378, 369–374, 375; 425/290, 363, 384, 388; 428/131, 132, 156, 35

[56] References Cited

U.S. PATENT DOCUMENTS

| D. 278,468 | 4/1985 | Trotman et al. | D92/1.1 |
|---|---|---|---|
| 810,120 | 1/1906 | Green . | |
| 2,273,542 | 2/1942 | Tasker . | |
| 3,156,242 | 11/1964 | Crowe, Jr. . | |
| 3,292,619 | 12/1966 | Egler . | |
| 3,371,667 | 3/1968 | Morse . | |
| 3,426,754 | 2/1969 | Bierenbaum et al. . | |
| 3,559,648 | 2/1971 | Mason, Jr. . | |
| 3,814,101 | 6/1974 | Kozak . | |
| 3,929,135 | 12/1975 | Thompson . | |
| 3,957,414 | 5/1976 | Bussey, Jr. et al. | 425/384 |
| 3,965,906 | 6/1976 | Karami . | |
| 3,966,383 | 6/1976 | Bussey, Jr. et al. | 425/388 |
| 3,979,494 | 9/1976 | Ericson | 264/154 |
| 3,989,867 | 11/1976 | Sisson | 428/132 |
| 3,994,299 | 11/1976 | Karami . | |
| 4,041,951 | 8/1977 | Sanford . | |
| 4,151,240 | 4/1979 | Lucas et al. | 264/504 |
| 4,155,693 | 5/1979 | Raley | 425/363 |
| 4,157,237 | 6/1979 | Raley | 425/363 |

List Continued on next page.

FOREIGN PATENT DOCUMENTS 845826  8/1960  United Kingdom .
1160625  8/1969  United Kingdom .

OTHER PUBLICATIONS

European Patent Application No. 101082A published 2/22/84.
European Patent Application No. 0 104 906 in the names of Patricia Eileen Becker and Kenneth John Molee, published 4/4/84.

List Continued on next page.

Primary Examiner—John D. Yasko
Attorney, Agent, or Firm—E. Kelly Linman; John V. Gorman; Richard C. Witte

[57] ABSTRACT

A macroscopically expanded, three-dimensional fluid-handling polymeric web having first and second surfaces located in substantially parallel planes which are remote from one another. The web includes a multiplicity of fluid-handling capillary networks of macroscopic cross-section for rapidly transmitting fluids which are dynamically deposited on the first surface of said web to the second surface of said web using the dynamic and gravitational head of the fluid as a primary driving force. Each of the macroscopic cross-section capillary networks originates as an aperture in the first surface of the web and has a continuously interconnected sidewall extending in the direction of the second surface of said web. The continuously interconnected sidewall terminates to form at least one aperture in the second surface of said web, whereby the bulk of the dynamically deposited fluid is transmitted from the first surface to the second surface of said web by the macroscopic cross-section capillary networks. The first surface of the web in which the macroscopic cross-section capillary networks originate further includes a multiplicity of fluid-handling capillary networks which are substantially smaller in cross-section than the macroscopic cross-section fluid-handling capillary networks. The smaller fluid-handling capillary networks exhibit a degree of capillary suction sufficient to transmit static fluid contained on the surface of objects which contact the first surface of said web generally in the direction of the second surface of said web by capillary attraction.

30 Claims, 30 Drawing Figures

U.S. PATENT DOCUMENTS

| | | | |
|---|---|---|---|
| 4,226,828 | 10/1980 | Hall | 264/555 |
| 4,248,822 | 2/1981 | Schmidt | 264/154 |
| 4,321,924 | 3/1982 | Ahr . | |
| 4,323,069 | 4/1982 | Ahr et al. . | |
| 4,327,730 | 5/1982 | Sorensen . | |
| 4,341,216 | 7/1982 | Obenour . | |
| 4,341,217 | 7/1982 | Ferguson et al. . | |
| 4,342,314 | 8/1982 | Radel et al. . | |
| 4,343,848 | 8/1982 | Leonard, Jr. | 428/156 |
| 4,351,784 | 9/1982 | Thomas et al. | 264/22 |
| 4,395,215 | 7/1983 | Bishop | 425/290 |
| 4,397,644 | 8/1983 | Matthews et al. | 604/378 |
| 4,463,045 | 7/1984 | Ahr et al. | 428/131 |
| 4,477,502 | 10/1984 | O'Sullivan | 428/35 |
| 4,508,256 | 4/1985 | Radel et al. | 228/152 |
| 4,509,908 | 4/1985 | Mullane, Jr. | 425/290 |
| 4,518,643 | 5/1985 | Francis | 428/131 |

OTHER PUBLICATIONS

UK Patent Application GB No. 2 103 933 in the name of George Howarth, published on 3/2/83.

UK Patent Application GB No. 2 021 479 in the names of Garland Eugene Raley and James Michael Adams, published on 12/5/79.

Commonly assigned, copending patent application Ser. No. 623,274, filed on June 21, 1984 in the name of Thomas Ward Osborne, III and entitled "Sanitary Napkin with Gross Foramina Overlying a Low Density, Resilient Structure."

Commonly assigned, concurrently filed, co-pending U.S. patent application Ser. No. 740,125 filed on 5/31/85 in the names of John J. Curro and E. Kelly Linman.

Commonly assigned, concurrently filed, co-pending U.S. patent application Ser. No. 740,145 filed on 5/31/85 in the names of John J. Curro, James C. Baird, Donald L. Gerth, George M. Vernon and E. Kelly Linman.

Commonly assigned, concurrently filed, co-pending U.S. patent application Ser. No. 740,112 filed on 5/31/85 in the name of Hugh A. Thompson.

Commonly assigned, concurrently filed, co-pending U.S. patent application Ser. No. 740,084 filed on 5/31/85 in the names of E. Kelly Linman, John J. Curro and E. Weinshenker.

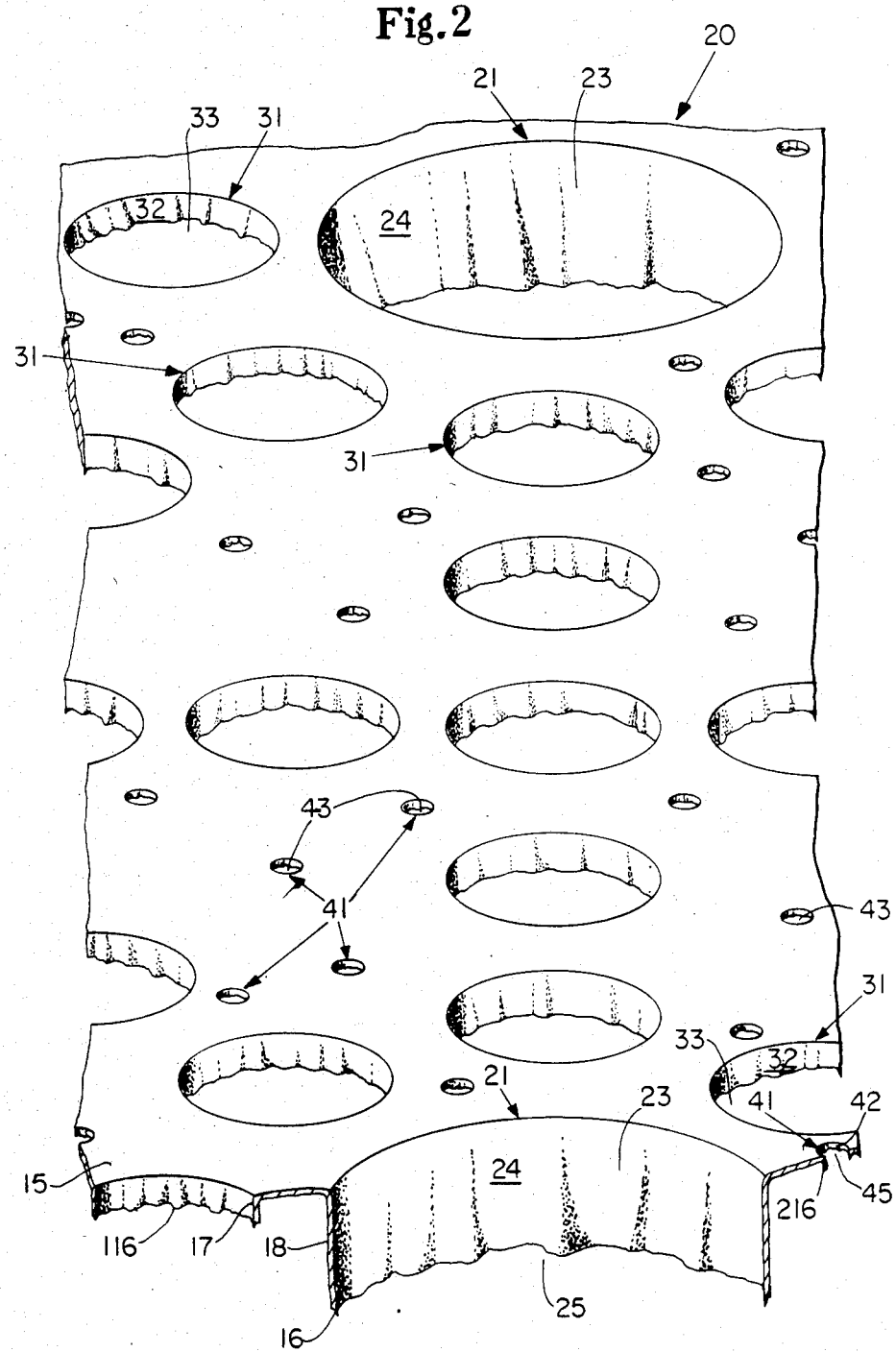

MACROSCOPICALLY EXPANDED THREE-DIMENSIONAL POLYMERIC WEB FOR TRANSMITTING BOTH DYNAMICALLY DEPOSITED AND STATICALLY CONTACTED FLUIDS FROM ONE SURFACE TO THE OTHER

TECHNICAL FIELD

The present invention has relation to macroscopically expanded three-dimensional polymeric webs containing capillary networks of differing size to effectively transmit both dynamically deposited fluids and statically contacted fluids from one surface thereof to the other.

The present invention has further relation to macroscopically expanded three-dimensional plastic webs which have been provided with relatively large capillary networks to transmit dynamically deposited fluids during high flow events such as urination, while the uppermost surface of the web in which the relatively large capillary networks originate, i.e., the body contacting portion of the web, is provided with a multiplicity of much smaller capillary networks to transmit static fluids which come in contact with the uppermost surface of the web to the opposite surface of the web by capillary attraction.

The present invention has further relation to the use of such webs as controlled fluid transfer membranes, e.g., as topsheets for disposable diapers, wherein the large capillary networks prevent or at least minimize lateral spreading of the deposited fluid by using the dynamic and gravitational head of the fluid to drive it through the large capillary networks and into an underlying absorbent substrate, while the small capillary networks in the portions of the web which contact the wearer's skin are sized to provide greater capillary suction than the wearer's skin. It is believed that when the smaller capillary networks are oriented oppositely from the large capillary networks so that they project outwardly from the absorbent substrate they act as tiny baffles. The baffle effect forces deposited fluids to undergo a more tortuous path to reach the edge of the absorbent device, thereby increasing the probability that the bulk of the fluid will enter one or more of the large capillary networks before reaching the edge of the absorbent device. It is further believed that the higher capillary suction provided by the smaller capillary networks in the web helps remove static moisture otherwise retained by the skin of the wearer, thus providing improved skin dryness.

The present invention has further relation to disposable absorbent bandage structures wherein the capillary suction of the smaller capillary networks in the macroscopically expanded three-dimensional plastic web lies intermediate that of the wearer's skin and that of the underlying absorbent substrate. This enables the absorbent substrate to rapidly remove the moisture from the smaller capillary networks of the topsheet, thereby providing a sustained skin drying action.

The present invention has still further relation to macroscopically expanded three-dimensional plastic webs having sufficient Z-direction caliper and resistance to becoming co-planar that contact between the wearer's skin and the underlying absorbent substrate is substantially prevented when said webs are subjected to compressive loadings typically caused by routine movements of the wearer.

BACKGROUND ART

It has long been known in the disposable absorbent bandage art that it is extremely desirable to construct absorptive devices, such as disposable diapers, sanitary napkins, incontinent devices, wound dressings, and the like, which are able to rapidly absorb discharged body fluids during high flow events, such as urination, without rapid spreading and leakage of the discharged fluids from the edges of the absorbent bandage structure. It is further recognized in the disposable absorbent bandage art that disposable absorbent bandage structures should present a dry surface feel to the user after the absorption process has been completed to improve wearing comfort and to minimize the development of undesirable skin conditions due to prolonged exposure to moisture.

Prior art web structures used as the wearer contacting surface on disposable bandages such as disposable diapers have been of two basic varieties, i.e., inherently fluid-pervious structures, such as fibrous nonwovens, and fluid-impervious materials such as polymeric webs which have been provided with a degree of fluid permeability via aperturing to permit fluid flow therethrough. Both varieties of prior art body contacting webs have been used in planar and in macroscopically expanded, three-dimensional configurations.

As utilized herein, the term "macroscopically expanded", when used to describe three-dimensional webs, ribbons and films, refers to webs, ribbons and films which have been caused to conform to the surface of a three-dimensional forming structure so that both surfaces thereof exhibit the three-dimensional pattern of said forming structure, said pattern being readily visible to the normal naked eye when the perpendicular distance between the viewer's eye and the plane of the web is not more than about 12 inches. Such macroscopically expanded webs, ribbons and films are typically caused to conform to the surface of said forming structures by embossing, i.e., when the forming structure exhibits a pattern comprised primarily of male projections, by debossing, i.e., when the forming structure exhibits a pattern comprised primarily of female capillary networks, or by extrusion of a resinous melt directly onto the surface of a forming structure of either type. Typically, it has been found that capillary networks having a maximum cross-sectional dimension of about 10 mils or more are visible to the normal naked eye at a perpendicular distance of about 12 inches. By way of contrast, the term "planar", when utilized herein to describe webs, ribbons and films, refers to the overall condition of the web, ribbon or film when viewed by the naked eye on a macroscopic scale. In this context "planar" webs, ribbons and films may include webs, ribbons and films having fine scale surface aberrations on one or both sides, said surface aberrations not being readily visible to the naked eye when the perpendicular distance between the viewer's eye and the plane of the web is about 12 inches or greater.

Due to the relatively small size of the random interstitial openings formed by the entangled fibers or fibrous nonwoven webs, fibrous nonwoven topsheets are not always capable of rapidly transmitting dynamically deposited fluids to an underlying absorbent substrate, particularly in situations where the fluids deposited are quite viscous, e.g., menses, liquid bowel movement, etc. This can lead to unsightly accumulations on the wearer contacting surface of the topsheet and, in extreme cases, leakage of these materials from the edges of the bandage with resultant soiling of the wearer's outer garments. In addition, although it has been observed that prior art fibrous nonwoven topsheets are, in general, effective in removing static moisture from the wearer's skin, their fluid pervious nature normally permits reverse flow to occur under compressive loading, thereby causing rewetting of the skin by an underlying moist absorbent substrate. This rewetting tendency is particularly pronounced with the planar topsheet structures. Accordingly, prior art efforts to solve these problems have led to the development of embossed, three-dimensional, fibrous nonwoven topsheets.

One such embossed, three-dimensional, fibrous nonwoven topsheet structure is disclosed in commonly assigned U.S. Pat. No. 4,041,951 issued to Sanford on Aug. 16, 1977 and hereby incorporated herein by reference. The Sanford patent discloses a preferred disposable diaper structure comprising a moisture absorbent layer disposed between a soft topsheet and a moisture resistant backing sheet. The nonwoven fibrous topsheet preferably comprises an integral structure containing a multiplicity of depressed areas which intimately contact the uppermost surface of the moisture absorbent layer. The nondepressed areas of the topsheet contact the wearer's skin in use. In a particularly preferred embodiment, the nonwoven fibrous topsheet is comprised of a substantially non-wetting material exhibiting wet resilience such that the topsheet tends to resume its substantially three-dimensional character upon removal of pressure applied against the topsheet by the body movements of the wearer. The void space provided by the depressed areas taught by Sanford helps to reduce leakage of rapidly deposited fluids, from the edges of the diaper, while the physical separation provided by the three-dimensionally and wet resilience of such a topsheet helps to prevent direct contact between the moist absorbent core and the wearer's skin under most circumstances. Nonetheless, the fluid-pervious nature of the nonwoven material may permit some rewetting of the skin when compressive loads sufficient to substantially collapse the three-dimensionality of the topsheet are experienced in use.

Other attempts to deal with the rewetting problem have involved the use of topsheets comprised of fluid-impervious material provided with various forms of apertures. For example, U.S. Pat. No. 3,814,101 issued to Kozak on June 4, 1974, suggests a topsheet of non-fibrous, hydrophobic film which is provided with a plurality of valvular slits which allegedly restrict the reverse flow of liquid from the absorbent element of the device.

Commonly assigned U.S. Pat. No. 3,929,135 issued to Thompson on Dec. 30, 1975, and hereby incorporated herein by reference, suggests a macroscopically expanded, three-dimensional topsheet comprised of liquid-impermeable material, but provided with tapered capillaries, said capillaries having a base opening in the plane of the topsheet and an apex opening remote from the plane of the topsheet, said apex opening being in intimate contact with the absorbent pad utilized in the disposable absorbent bandage. Fluids deposited on the wearer contacting surface of the topsheet are freely transferred to the absorbent substrate, while flow in the reverse direction is inhibited by the decreasing cross-section of the tapered capillaries.

Still another material which has been utilized as a body contacting surface in a disposable absorbent bandage context is disclosed in commonly assigned U.S. Pat. No. 4,342,314 issued to Radel et al. on Aug. 3, 1982, and hereby incorporated herein by reference. The commonly assigned Radel et al. patent discloses an improved macroscopically expanded three-dimensional plastic web exhibiting a fine-scale three-dimensional microstructure comprising a regulated continuum of capillary networks originating in and extending from one surface of the web and terminating in the form of apertures in the opposite surface thereof. In a preferred embodiment, the capillary networks are of decreasing size in the direction of liquid transport. The web's fiber-like appearance is comprised of a continuum of fiber-like elements of substantially uniform U-shaped cross-section, each end of said fiber-like elements being interconnected to at least one other of said fiber-like elements. In a particularly preferred embodiment, the interconnected fiber-like elements are substantially non-aligned with respect to one another to enhance the fiber-like appearance.

While macroscopically expanded three-dimensional plastic webs of the type generally described in the aforementioned commonly assigned Thompson and Radel et al. patents have met with good success in permitting rapidly discharged body fluids, such as urine, to be transmitted from the surface on which they are initially deposited to an underlying absorbent core element with little or no leakage from the edges of the bandage structure, it has been observed that the wearer's skin may still look and feel moist upon removal of the bandage from the wearer's body. Since it can be quantitatively demonstrated that macroscopically expanded three-dimensional plastic webs of the type disclosed in the aforementioned patents to Thompson and Radel et al. are highly effective in preventing rewetting of the wearer's skin once discharged body fluids have passed into the underlying absorbent substrate, it is believed that much of the moisture remaining on the wearer's skin when absorbent structures employing topsheets of this type are removed from the wearer's body is not due to rewetting from the underlying moist absorbent core. Rather, it is believed that this fluid contacts the skin during the period or periods of high volume discharge and is simply never removed from the wearer's skin after the bulk of the fluid discharge has been transmitted to the absorbent substrate through the macroscopic cross-section capillary networks in the web. This is believed due to the low capillary suction exhibited by the macroscopic cross-section capillary networks in the web in relation to the relatively high capillary suction exhibited by the wearer's skin.

Accordingly, it is a principal object of the present invention to provide a macroscopically expanded, three-dimensional polymeric web with precisely controlled fluid transfer characteristics tailored not only to the fluid, but also to the range of flow conditions anticipated in use.

It is another object of the present invention to provide a macroscopically expanded, three-dimensional polymeric web which exhibits an ability to transmit rapidly deposited body fluid discharges through capillary networks of macroscopic cross-section to an underlying absorbent substrate, which is resistant to becoming co-planar under compressive loading, and which exhibits an ability to dry the wearer's skin of moisture remaining in contact with the skin once the bulk of the rapidly discharged fluid has been transmitted to the absorbent core of the structure.

It is another object of the present invention to provide such a web wherein the body contacting surface of the web in which the capillary networks of macroscopic cross-section originate is provided with a multiplicity of capillary networks which are substantially smaller in cross-section, said smaller capillary networks exhibiting sufficient capillary suction to transmit static fluid from moist objects which contact the surface of the web generally in the direction of an underlying absorbent substrate by capillary attraction.

It is still another object of the present invention to provide such a web, wherein said smaller capillary networks are oriented outwardly from the absorbent substrate to create a tortuous path which deposited liquids must follow to reach on edge of the absorbent device, thereby increasing the probability that the bulk of the deposited fluid will enter one or more of the large capillary networks before reaching the edge of the absorbent device.

DISCLOSURE OF INVENTION

The present invention pertains, in a particularly preferred embodiment, to a macroscopically expanded three-dimensional fluid handling polymeric web having first and second surfaces located in substantially parallel planes which are remote from one another. The web includes a multiplicity of fluid handling capillary networks of macroscopic cross-section for rapidly transmitting fluids which are dynamically deposited on the first surface of the web to the second surface of the web using the dynamic and gravitational head of the fluid as the primary driving force. Each of the macroscopic cross-section capillary networks originates as an aperture in the first surface of the web and has a continuously interconnected sidewall extending in the direction of the second surface of the web. The continuously interconnected sidewall terminates to form at least one aperture in the second surface of the web, whereby the bulk of any dynamically deposited fluid is transmitted from the first surface to the second surface of the web by the macroscopic cross-section capillary networks. The first surface of the web in which the macroscopic cross-section capillary networks originate further includes a multiplicity of fluid handling capillary networks which are substantially smaller in cross-section and normally substantially smaller in overall length than the macroscopic cross-section fluid handling capillary networks. These smaller capillary networks may be oriented inwardly toward the absorbent substrate outwardly away from said absorbent substrate. These smaller fluid handling capillary networks exhibit a degree of capillary suction sufficient to transmit static fluid contained on the surface of objects which contact the first surface of the web generally in the direction of the second surface of the web by capillary attraction.

When used as a body contacting topsheet in the context of a disposable absorbent bandage, such as a disposable diaper, the smaller fluid handling capillary networks in the first surface of the web are sized to provide a greater capillary suction than the wearer's skin. The use of such a body contacting topsheet in conjunction with an underlying absorbent substrate which exhibits an even greater capillary suction than the small capillary networks in the first surface of the web provides a one-way driving force which tends to dry the skin of static moisture, while the resilient three-dimensional nature of the web substantially prevents rewetting of the skin when the web is subjected to compressive loading due to body movements of the wearer. Thus macroscopically expanded, three-dimensional polymeric webs of the present invention retain the gush handling and anti-rewet capabilities of prior art polymeric webs of the type generally disclosed in the aforementioned commonly assigned patents to Thompson and to Radel et al. However, they, in addition, can provide precisely engineered skin drying capabilities, a benefit previously obtainable, if at all, only on a limited basis by empirical selection of particular fibrous webs.

In those web embodiments wherein the smaller capillary networks are oriented outwardly away from the absorbent substrate, they tend to act as tiny baffles which force deposited fluids to undergo a tortuous path to reach an edge of the absorbent device. As a result, a greater portion of the deposited fluid passes into the large capillary networks before it can reach an edge of the absorbent device. This results in reduced leakage from the absorbent device. A secondary benefit afforded by the outwardly oriented smaller capillary networks is that the tiny apertured ends of the smaller capillary networks provide a softer, more comfortable wearer contacting surface.

Preferred methods and apparatus for forming said macroscopically expanded, three-dimensional polymeric webs are also disclosed.

BRIEF DESCRIPTION OF THE DRAWINGS

While the specification concludes with claims particularly pointing out and distinctly claiming the present invention, it is belived the present invention will be better understood from the following description in which:

FIG. 2 is a greatly enlarged, simplified perspective illustration of a segment of macroscopically expanded three-dimensional polymeric web suitable for use as a topsheet in a disposable diaper such as that shown in FIG. 1;

DETAILED DESCRIPTION OF THE INVENTION

While the present invetion will be described in the context of providing a macroscopically expanded, three-dimensional, resilient polymeric web suitable for use as a topsheet on an absorbent bandage such as a disposable diaper or the like, the present invention is in no way limited to such application. The present invention may in fact be practiced to great advantage in many situations where it is desired to transmit fluids which are either dynamically deposited on or which statically contact one surface of the web to its opposite surface and to prevent or at least minimize flow in the reverse direction. The detailed description contained herein which relates to a preferred structure and its use as a topsheet which in a disposable diaper will allow one skilled in the art to readily adapt the invention to other devices.

Figure 1:
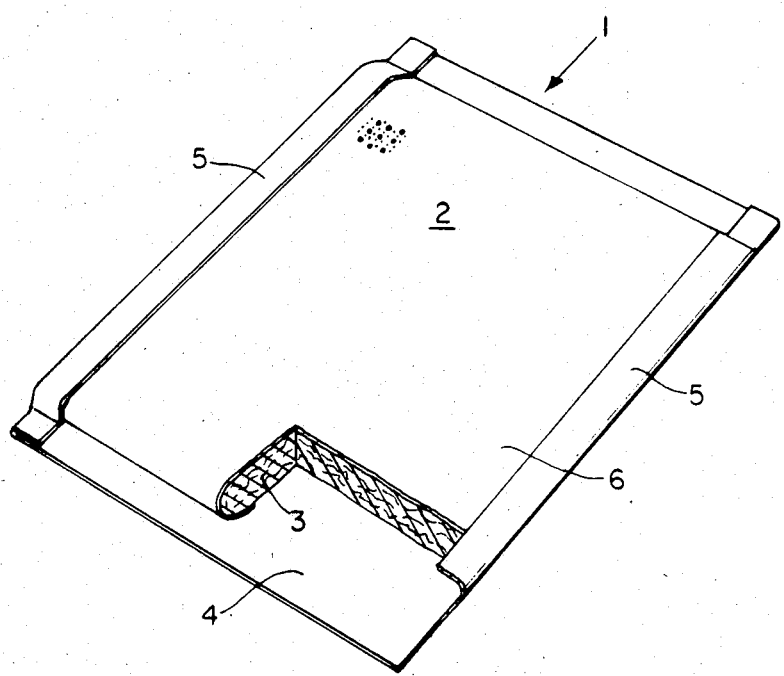
FIG. 1 is a simplified perspective representation of an unfolded disposable diaper employing a web of the present invention as a body contacting topsheet with portions of its components cut away.

FIG. 1 is a perspective view of a disposable absorbent bandage comprising a diaper in an unfolded condition. Various layers have been cut away to more clearly show the structural details of this embodiment. The disposable diaper is referred to generally by the reference numeral 1. A fluid pervious topsheet of the present invention is shown at 2. The other two major components of the disposable diaper 1 are the absorbent element or pad 3 and the fluid-impervious backsheet 4. In general, the side flaps 5 of the backsheet 4 are folded so as to cover the edges of the absorbent pad 3 and topsheet 2. Topsheet 2 is generally folded to completely enclose the ends of the absorbent pad 3. The drawing of diaper 1 in FIG. 1 is a simplified representation of a disposable diaper. A more detailed description of a preferred embodiment of a disposable diaper is contained in commonly assigned U.S. Pat. No. 3,952,745 issued to Duncan on Apr. 27, 1976, said patent being hereby incorporated herein by reference.

As will be appreciated by those skilled in the art, the precise performance parameters for the disposable absorbent bandage generally shown in FIG. 1 will depend upon the use to which the structure is to be put. For example, if the structure is to be utilized as an infant diaper, it has been observed that urine discharge flow rates on the order of 6-12 millileters per second and voidings on the order of 20-120 millileters per discharge are not uncommon. If, on the other hand, the disposable absorbent bandage is to be employed as an adult incontinent brief, urine discharge flow rates on the order of 10-25 millileters per second and voidings on the order of 100-500 millileters per discharge may often be encountered. As will be hereinafter pointed out in greater detail, the gush flow handling characteristics of the topsheet 2 can be scaled upwardly or downwardly, as appropriate, to permit rapid transmission of dynamically deposited fluids to the underlying absorbent substrate without significant leakage from the edges of the bandage.

In addition to varying flow rate considerations for any given fluid, the design of a body contacting topsheet must also take into account the type or types of material to be transmitted from one surface of the web to the other and the differing flow rates for the different materials. For example, urine typically has a viscosity on the order of about one centipose at normal ambient temperatures. If, however, the topsheet is also intended to transmit liquid bowel movement into an underlying absorbent substrate for long term retention, viscosities are often in the 50-1400 centipose range. For infants, discharge flow rates for the latter material are often on the order of 15 millileters per second, with voidings on the order of 90 millileters per discharge. On the other hand, if topsheets of the present invention are to be employed in disposable absorbent products such as sanitary napkins, wherein menses is the primary fluid to be absorbed, viscosities in the range of 5-50 centipose are common. Discharge flow rates for menses are often on the order of about 3 millileters per second, with voidings on the order of 5 millileters per discharge.

When macroscopically expanded, three-dimensional, apertured polymeric webs of the type generally disclosed in FIG. 6C of the aforementioned commonly assigned patent to Radel et al. are employed as a topsheet for an infant diaper, it has been observed that leakage from the edges of the diaper can be substantially prevented during typical infant urine voiding situations. An exemplary topsheet of the aforementioned type exhibited an open area provided by the macroscopic cross-section capillary networks totaling about 35 percent of the web's body contacting surface, each of said capillary networks exhibiting pentagonally shaped macroscopic cross-section capillary networks having a maximum cross-sectional dimension on the order of about 30 mils.

Despite their ability to handle such gush flow situations, diapers utilizing such topsheets still reveal static moisture in contact with the wearer's skin upon removal of the diaper from the wearer's body. As pointed out earlier herein, it is believed that the moisture present on the wearer's skin is not due to rewetting from the moist underlying absorbent core, but rather to the higher capillary suction exhibited by the wearer's skin when contrasted to the relatively low capillary suction exhibited by the much larger macroscopic cross-section capillary networks present in the macroscopically expanded three-dimensional polymeric web. It is believed that the higher capillary suction of the skin prevents the macroscopic cross-section capillary networks in the web from removing this moisture from the wearer's skin after voiding has occurred.

FIG. 2 discloses one preferred embodiment of a macroscopically expanded, three-dimensional, apertured polymeric web 20 of the present invention. Web 20 is particularly suitable as a starting material for topsheet 2 in a disposable diaper such as that illustrated in FIG. 1.

Macroscopically expanded, three-dimensional, apertured polymeric web 20 exhibits a multiplicity of cylindrical capillary networks 21 and 31 which, when viewed from overhead, are of macroscopic cross-section, i.e., they are visually perceivable by the normal human eye when viewed at a perpendicular distance not exceeding about twelve inches. As can be seen in FIG. 2, macroscopic capillary networks 21 are generally larger than macroscopic capillary networks 31. This difference in size is not a requirement of the present invention, but is illustrated merely to reflect that the size of all macroscopic capillary networks need not be identical across the entire surface of the web 20. It is, however, recognized that in those situations where different fluid materials are likely to be encountered, macrosopic cross-section capillary networks of differing size may be preferred.

In general, the size of any particular macroscopic capillary network should be sufficiently large that the principal driving force for transmitting dynamically deposited fluids from the first surface 15 of the web 20 to the second surface 16 is provided by the dynamic and gravitational head of the fluid rather than capillary suction exhibited by the geometry of the network.

As can be seen in FIG. 2, each macroscopic cross-section capillary network 21 originates as an aperture 23 in the first surface 15 of the web. Each aperture 23 is placed is fluid communication with a second aperture 25 located in the second surface 16 of the web by means of a continuously interconnected sidewall 24. The arrangement is similar with respect to each of the macroscopic cross-section capillary networks 31 which originate as an aperture 33 in the first surface 15 of the web and which are connected to an aperture 35 in tertiary surface 116 of the web by means of a continuously interconnected sidewall 32.

As has been pointed out earlier herein, macroscopic cross-section capillary networks 21 and 31 function to handle gush flow situations, i.e., fluids rapidly deposited onto the uppermost surface 15 of the web are transmitted via the larger networks 21 and 31 to an underlying absorbent substrate without substantial leakage from the edges of the absorbent bandage to which the topsheet is secured. By way of contrast, the smaller capillary networks 41 located in first surface 15 of web 20 are of such small cross-section that they do not function appreciably in gush flow situations to transmit significant quantities of rapidly discharged fluid directly to the underlying absorbent substrate. Rather, capillary networks 41, which originate as relatively small apertures 43 in surface 15 of the web, extend a relatively short distance toward the secondary and tertiary surfaces 16 and 116, respectively, of the web 20, i.e., each continuously interconnected sidewall 42 may be only slightly greater in overall length, as measured along the longitudinal axis of the network, than the initial thickness of the planar film or polymer melt from which the macroscopically expanded three-dimensional web 20 is formed. As can be seen in FIG. 2, sidewalls 42 of capillary networks 41 terminate to form apertures 45 in quaternary surface 216 of web 20.

As will be appreciated by those skilled in the art, the first and second surfaces, 15 and 16, respectively, of web 20 are preferably separated from one another a distance sufficient to prevent contact between the wearer's body and the underlying absorbent substrate even when compressive loadings on the order of about one-half to about one pound per square inch are exerted upon the web 20. (Experience has demonstrated compressive loadings of this magnitude may be exerted on the web due to movements of the wearer's body in activities such as sitting.) As with polymeric webs of the type disclosed in the aforementioned commonly assigned patents to Thompson and Radel et al., this resistance to becoming co-planar is also desirable in webs of the present invention to prevent rewetting of the skin by fluids which have already been absorbed into the absorbent substrate.

However, unlike macroscopically expanded, three-dimensional, apertured polymeric webs of the prior art, polymeric webs of the present invention also exhibit a multiplicity of much smaller capillary networks in the body contacting surface of web. It has been found that these small capillary networks 41, if properly sized and positioned adjacent an absorbent substrate exhibiting an even higher capillary suction, compete very effectively with the wearer's skin to remove moisture remaining on the skin's surface.

As will be appreciated by those skilled in the art, capillary networks 41 need not be cylindrical, as shown in FIG. 2, to function in the intended manner. They can be either regular or irregular in shape, and will still function in the intended manner, provided they are of the proper size range, shape and surface chemistry. If, for purposes of this specification, the cross-sectional shape of the capillary network is defined by a major axis which coincides with the maximum cross-sectional dimension of the network and a minor axis which coincides with the minimum cross-sectional dimension of the network, as measured perpendicular to the major axis of the network, the minor axis will normally be controlling in defining the capillary suction of the particular network. In this regard it has been observed that when the minor axis of the network is less than about 10 mils (0.010 inches), the capillary network will compete very effectively for urine in static contact with the wearer's skin. For minor axis dimensions between about 10 mils and 20 mils, there is a tapering off of the network's capillary suction. Accordingly, skin drying capillary networks such as 41 preferably exhibit a minor axis dimension in the range of about 10 mils or less while macroscopic cross-section capillary networks such as 21 and 31 preferably exhibit a minor axis dimension on the order of about 20 mils or greater.

While it is generally desirable that macroscopic capillary networks 21 and 31 exhibit a relatively large minor axis dimension to present the greatest cross-sectional flow area to fluids which are dynamically deposited on the uppermost surface 15 of web 20, the upper limit on the dimension of the minor axis is determined primarily on the basis of rewet considerations. That is, for macroscopic capillary networks having very large minor axis dimensions, there will be greater opportunity for the underlying absorbent substrate and the wearer's skin to contact one another as the web 20 is subjected to greater and greater compressive loads. Accordingly, the upper limit dimension for the minor axis of the macroscopic cross-section capillary networks is normally chosen on the basis of preventing contact between the absorbent substrate and the wearer's skin under the range of compressive loadings anticipated for a particular environment.

Similarly, the density and spacing of the macroscopic capillary networks 21 and 31 relative to one another will depend primarily upon the anticipated in use flow conditions.

It is also possible in practicing the present invention to provide dual purpose capillary networks which combine the functions of the smaller capillary networks and the macroscopic cross-section capillary networks in a single passageway. Examples might include star-shaped passageway, wherein the points of the star behave in a manner similar to the smaller capillary networks, while the centrally located portions of the star behave in a manner similar to the macroscopic cross-section capillary networks. Other examples of such dual purpose passageways might include snowflake shaped passageways, dogbone shaped passageways and the like.

In general, it has been found that to provide adequate physical isolation and rewet protection between an underlying moist absorbent substrate and the wearer's skin, a physical separation between the first and second surfaces, i.e., the perpendicular distance between surfaces 15 and 16 of web 20, is preferably at least about 7-10 mils, most preferably at least about 15 mils. As will be appreciated from an inspection of FIG. 2, the separation between surfaces 15 and 16 is established by the overall length of the macroscopic capillary network sidewalls 24. In general, the sidewall length will be on the order of half the major axis dimension of the largest capillary network, as measured along the longitudinal axis of the network. This is due to the fact that if the effects of material thinning during the macroscopic expansion process are ignored, the material comprising the capillary network sidewall 24 is that which initially occupied the area framed by aperture 23 prior to macroscopic expansion of the web. From the foregoing, it will be understood that for macroscopic cross-section capillary networks having smaller major and minor axis dimensions, e.g., capillary networks 31, a tertiary surface 116 will be established in a plane oriented parallel to and located intermediate surfaces 15 and 16. The same is also true with respect to the much smaller capillary networks 41 which establish a quaternary surface 216 in a plane oriented parallel to and located intermediate surfaces 15 and 116. In general, a new surface remote from and parallel to first surface 15 will be established for each set of capillary networks having a distinct size and shape. Thus, there will be as many intermediate surfaces in web 20 as there are different size and shape capillary networks originating in web surface 15.

Figure 2A:
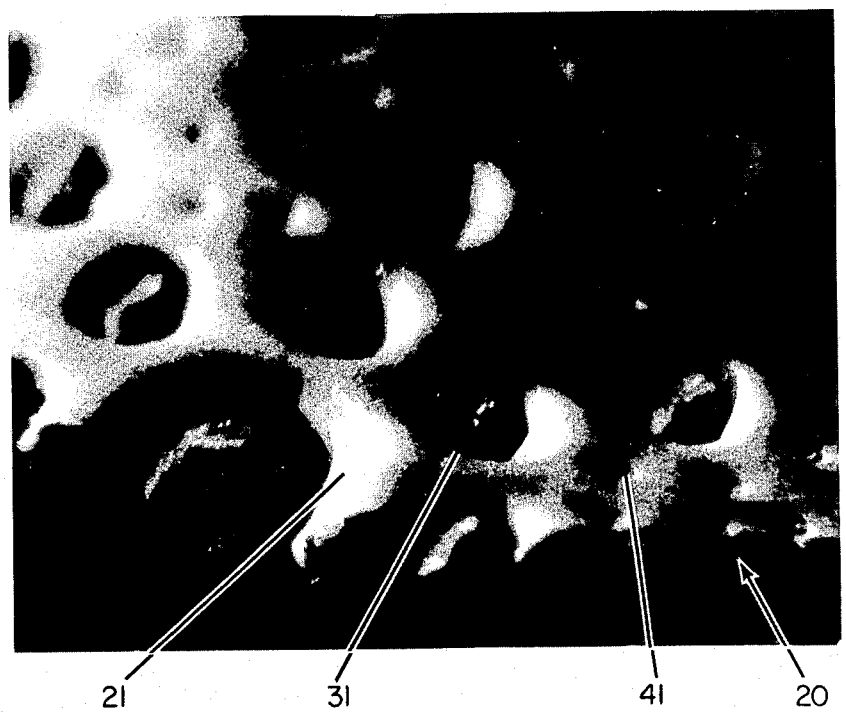
FIG. 2A is a greatly enlarged, perspective photograph of a segment of a macroscopically expanded three-dimensional polymeric web of the type generally illustrated in FIG. 2.

FIG. 2A is a greatly enlarged perspective view photograph of an actual web sample 20 of the type generally illustrated in FIG. 2.

Figure 3:
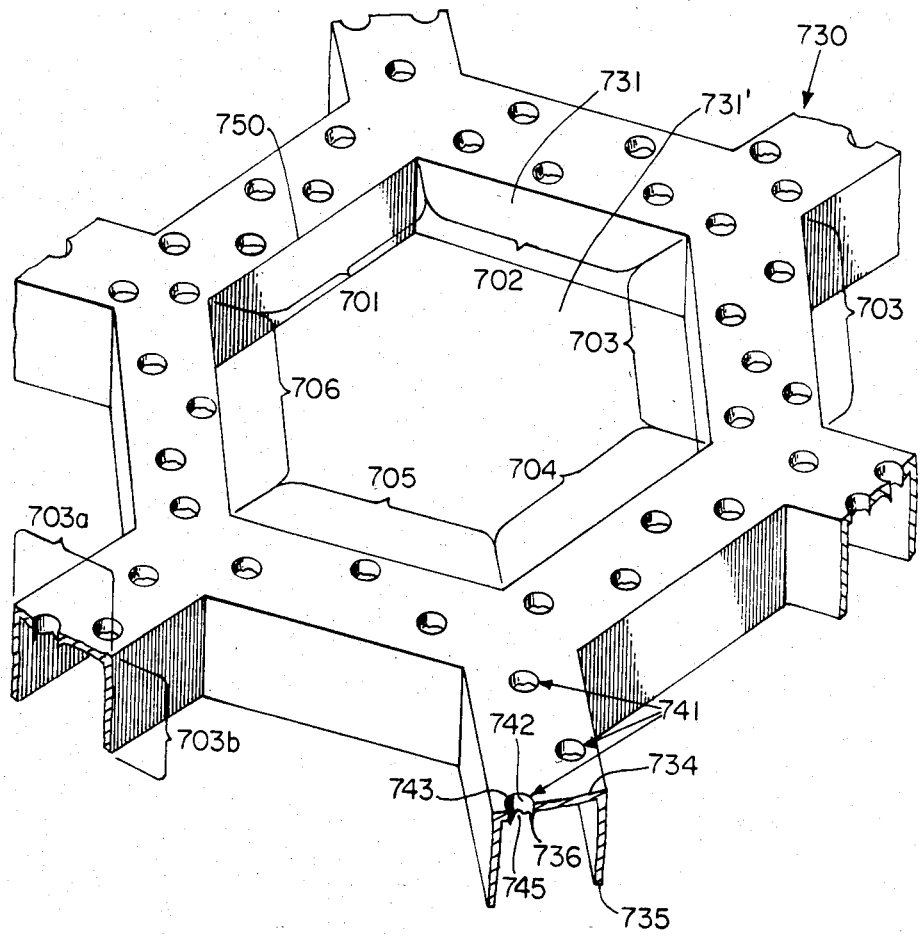
FIG. 3 is a greatly enlarged, simplified perspective illustration of an alternative macroscopically expanded, three-dimensional polymeric web of the present invention.

FIG. 3 depicts an alternative embodiment of a macroscopically expanded three-dimensional polymeric web 730 of the present invention. The web 730 depicted in FIG. 3 is a fiber-like web similar to the one generally illustrated and described in connection with FIG. 6C of commonly assigned U.S. Pat. No. 4,342,314 issued to Radel et al. on Aug. 3, 1982, and incorporated herein by reference. Web embodiment 730 exhibits a multiplicity of apertures, e.g., apertures 731, each formed by a multiplicity of intersecting fiber-like elements of generally U-shaped cross-section, e.g., elements 701, 702, 703, 704, 705 and 706, interconnected to one another in the first surface 734 of the web. Each fiber-like element comprises a base portion, e.g, base portion 703a, located in first surface 734. Each base portion has a sidewall portion, e.g., sidewall portions 703b, attached to each edge thereof. The sidewall portions extend generally in the direction of the second surface 735 of the web. The intersecting sidewall portions of the fiber-like elements are interconnected to one another intermediate the first and second surface of the web, and terminate substantially concurrently with one another in the second surface 735 of the web to form apertures 731'. The sidewall portions of the fiber-like elements may be oriented substantially perpendicular to the base portion of the elements or they may be angled with respect to the base portion, thereby producing apertures 731' in the second surface 735 of the web which are smaller than the apertures 731 in the first surface 734 of the web. In the latter case each resultant capillary network 750 formed by each set of interconnected sidewall portions is of decreasing cross-section in the direction of the second surface.

Despite the foregoing similarities, web 730 of the present invention differs from the fiber-like web disclosed in FIG. 6C of the aforementioned Radel et al. patent in one important regard. Namely, its uppermost surface 734 contains a multiplicity of relatively small cylindrical capillary networks 741 originating as apertures 743 in surface 734, said apertures being interconnected by means of continuously interconnected sidewalls 742 to apertures 745 in tertiary web surface 736.

As with the web embodiments shown in FIGS. 2 and 2A, web embodiment 730 transmits dynamically deposited fluids from its uppermost surface 734 to its lowermost surface 735 via the multiplicity of macroscopic cross-section capillary networks 750 formed by intersecting fiber-like elements 701, 702, 703, 704, 705, 706, etc. The smaller capillary networks 741, on the other hand, are preferably of a size similar to the smaller capillary networks 41 in web embodiment 20 shown in FIGS. 2 and 2A. Accordingly, they are able to effectively compete for moisture remaining on the surface of objects contacting web surface 734 and to transmit such moisture in the direction of web surface 736 and the underlying absorbent substrate by means of capillary attraction.

Figure 6:
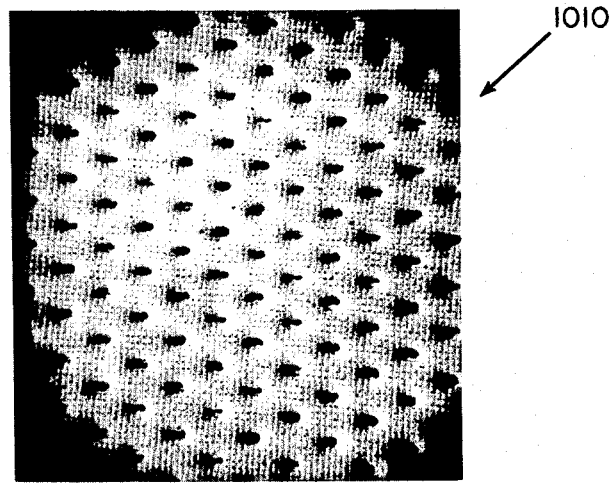
FIG. 6 is a greatly enlarged, plan view photograph of an alternative macroscopically expanded, three-dimensional polymeric web of the present invention.

Macroscopically expanded, three-dimensional polymeric web embodiments of the type generally shown in FIGS. 2, 2A and 3 can be made in accordance with any of the process embodiments shown in FIGS. 6, 8 and 9 of the co-pending, commonly assigned patent application of John J. Curro, James C. Baird, Donald L. Gerth, George M. Vernon and E. Kelly Linman entitled MULTI-PHASE PROCESS FOR DEBOSSING AND PERFORATING A POLYMERIC WEB TO COINCIDE WITH THE IMAGE OF ONE OR MORE THREE-DIMENSIONAL FORMING STRUCTURES, Ser. No. 740,145 filed May 31, 1985, now U.S. Pat. No. 4,609,518, said patent application being concurrently filed herewith and hereby incorporated herein by reference.

Figure 4:
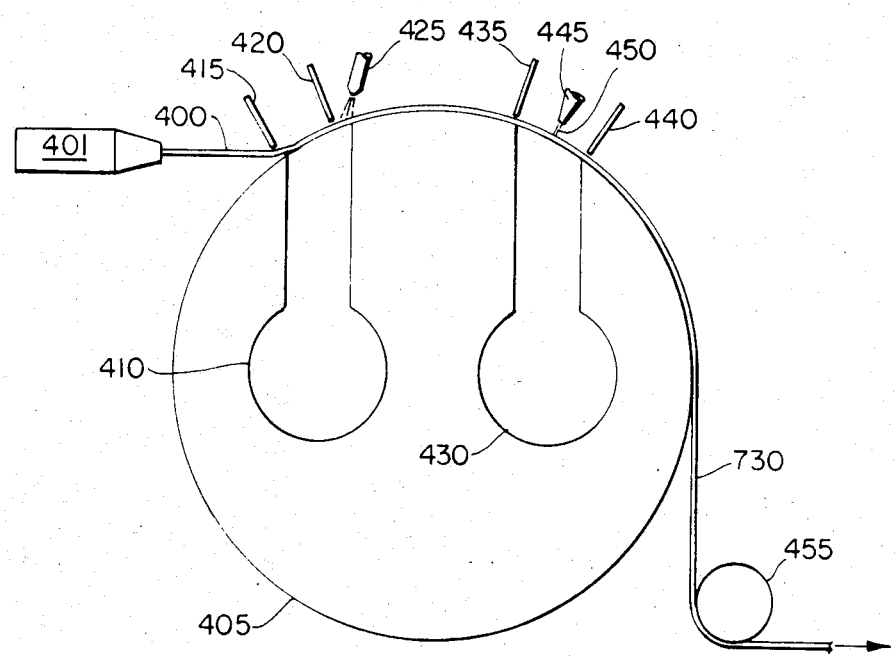
FIG. 4 is a simplified schematic illustration of a preferred process which may be utilized to produce macroscopically expanded three-dimensional polymeric webs of the present invention.

One such preferred process for producing a macroscopically expanded, three-dimensional, apertured polymeric web of the present invention is schematically illustrated in simplified form in FIG. 4. Basically, the preferred process is initiated by extruding a polymeric melt 400 from a conventional extruder 401 onto a three-dimensional forming structure made in a manner similar to that taught by commonly assigned U.S. Pat. No. 4,342,314 issued to Radel et al. on Aug. 3, 1982, and incorporated herein by reference.

The three-dimensional forming structure 405 traverses a first fluid pressure differential zone preferably comprising a stationary vacuum chamber 410. The sub-atmospheric pressure existing within vacuum chamber 410 causes the heated polymeric melt 400 to three-dimensionally conform to the surface of the forming structure 405 and thereafter apertures the macroscopic cross-section capillary networks thus formed. A baffle 415 prevents the polymeric melt 400 from being disturbed by fast moving air which is drawn into vacuum chamber 410 once aperturing of the polymeric melt 400 occurs. To ensure that the macroscopically expanded three-dimensional geometry imparted by the vacuum is maintained in the web, the temperature of the web is rapidly lowered while the web is still subject to the forming vacuum, preferably by a low pressure, e.g., less than about 50 psig, cold water spray. This is preferably accomplished by means of a low pressure spray nozzle 425 which, in conjunction with baffle 420, forms a small pool of cooling water which is drawn into the trailing portion of vacuum chamber 410 by gravity and the sub-atmospheric pressure existing therewithin. Lowering the temperature of the web before it passes the trailing edge of vacuum chamber 410 helps to prevent spring-back of the wb with consequent loss of caliper and closing of some of the apertures created therein. Although the water assisted cooling is generally not required at speeds below about 50 feet per minute, this water assisted cooling operation facilitates operation of the process at much higher speeds without adverse effects. Details of the foregoing water assisted cooling operation are more fully set forth in the commonly assigned co-pending patent application of Thurman J. Koger, II, Theodore E. Farrington, Jr. and Eugene Weinshenker, Ser. No. 549,525, entitled PROCESS FOR HIGH SPEED PRODUCTION OF WEBS OF DEBOSSED AND PERFORATED THERMOPLASTIC FILM, filed on Nov. 4, 1983, issued on Nov. 12, 1985 as U.S. Pat. No. 4,552,709 and hereby incorporated herein by reference.

Figure 5:
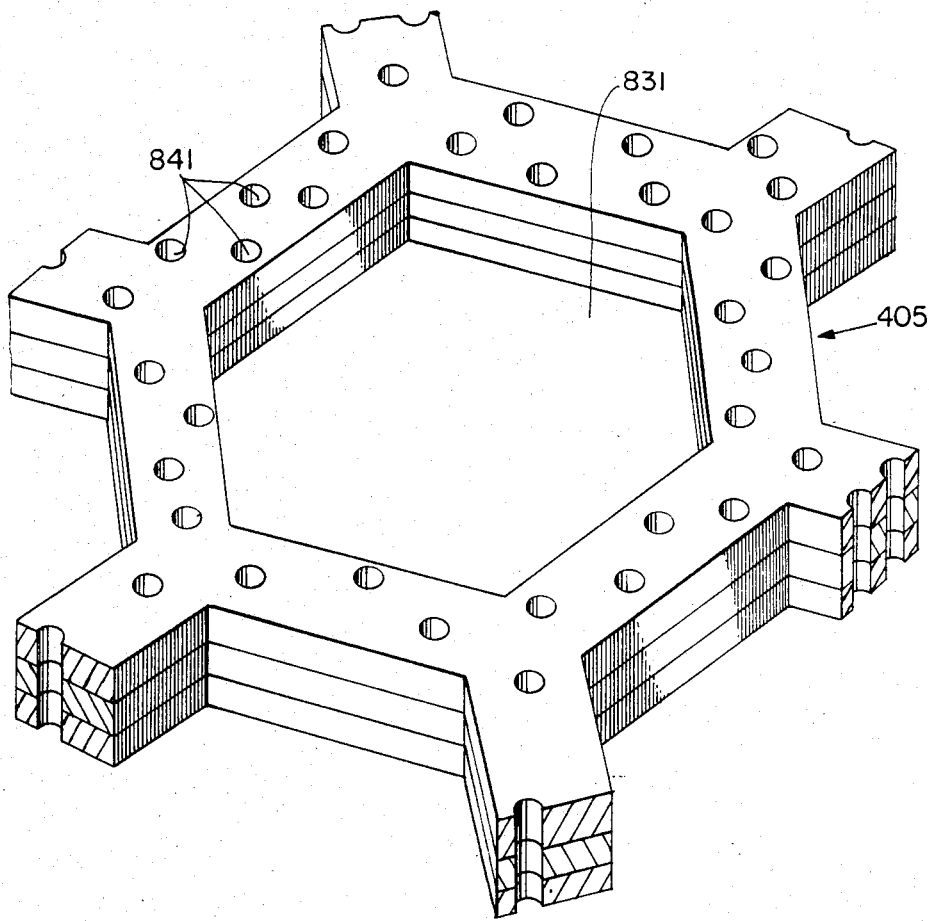
FIG. 5 is a greatly enlarged perspective illustration of a segment of a forming structure suitable for producing a polymeric web such as that shown in FIG. 3 using a process such as that schematically illustrated in FIG. 4.

Upon completion of the water assisted cooling phase of the process generally illustrated in FIG. 4, the macroscopically expanded three-dimensional plastic web has, with one important exception which will be hereinafter described, a three-dimensional shape generally corresponding to that of forming structure 405 illustrated in greatly enlarged form in FIG. 5. Aperture 731' in surface 735 of web 730 corresponding to apertures 831 in forming structure 405 have, by this point in time, been formed by the action of the vacuum chamber 410. However, due to the presence of the large apertures 731' and the relatively small size of apertures 841 in forming structure 405, the application of suction by vacuum chamber 410 is normally not sufficient to cause rupture of those portions of the polymeric web coinciding with apertures 841 in the forming structure. Accordingly, the macroscopically expanded, three-dimensional plastic web does not, at this point, include the smaller capillary networks 741.

Therefore, the web is retained on forming structure 405 at least until it reaches secondary low pressure vacuum chamber 430, the leading and trailing ends of which coincide with baffles 435 and 440 respectively. Between the baffles 435 and 440 there is provided a high pressure, i.e., generally in the range of about 400 to about 1200 psig, water jet nozzle 445 extending across the width of the web, or at least so much of the three-dimensionally expanded web as is to be finely apertured. Because of the much higher pressure of the water jet, particularly when compared to the forces applied to the web by vacuum chamber 410, the web is fully conformed and fully apertured in the image of the forming structure. This provides fully apertured capillary networks 741 in those portions of web 730 coinciding with apertures 841 in forming structure 405.

If the effects of film thickness are ignored, substantially all of the apertures, i.e., macroscopic apertures 831 and smaller sized apertures 841, contained in forming structure 405 produce corresponding capillary networks of similar size and shape in the resultant macroscopically expanded, three-dimensional, apertured polymeric web 730.

The water used to produce fine scale capillary networks 741 in the polymeric web is preferably collected inside vacuum chamber 430 and is recycled, by means of suitable separating apparatus (not shown) to a high pressure pump which redelivers the water under pressure to nozzle 445.

The aforementioned water jet process is described in greater detail in the commonly assigned copending patent application of John J. Curro, Alan J. Trusty and George M. Vernon entitled FORMED MATERIAL PRODUCED BY SOLID-STATE FORMATION WITH A HIGH PRESSURE LIQUID STREAM, Ser. No. 580,911, filed Feb. 16, 1984 and hereby incorporated herein by reference.

The resultant macroscopically expanded, three-dimensional polymeric web 730 is thereafter removed from the surface of the forming structure 405 by feeding it about idler roll 455, after which it may be directed to further processing operations (not shown) or to a suitable rewind station (not shown).

Figure 7:
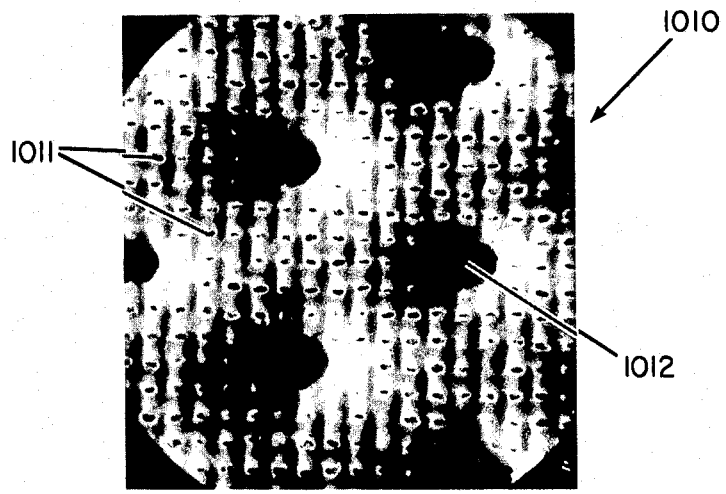
FIG. 7 is a further enlarged photograph of the web shown in FIG. 6.

FIGS. 6 and 7 are plan view photographs, enlarged many times actual size, of an alternative web embodiment 1010 of the present invention said web exhibiting a fine-scale pattern of upwardly oriented, apertured capillary networks 1011, the edges of which end in silky feeling cusps. The web 1011 may be produced generally in accordance with the process embodiment disclosed in FIG. 1 of the commonly assigned co-pending U.S. patent application of John J. Curro, James C. Baird, Donald L. Gerth, George M. Vernon and E. Kelly Linman entitled MULTI-PHASE PROCESS FOR DEBOSSING AND PERFORATING A POLYMERIC WEB TO COINCIDE WITH THE IMAGE OF ONE OR MORE THREE-DIMENSIONAL FORMING STRUCTURES, Ser. No. 740,145, filed concurrently herewith and incorporated herein by reference. Because the entire surface of the web is subjected to fine scale aperturing on a first forming structure prior to undergoing macroscopic expansion and large scale aperturing in the opposite direction on a second forming structure, these tiny capillary networks 1011 are present both in the non-debossed land areas of the film as well as in the capillary sidewalls of the macroscopic cross-section capillary networks 1012. Due to the tactile impression imparted to the web by cusps of the small capillary networks 1011, web 1010 is normally perceived as well suited for sustained contact with the skin. Furthermore, because of the great disparity in cross-sectional size between the macroscopic cross-section capillary networks 1012 and the smaller capillary networks 1011, films of the type generally shown in FIGS. 6 and 7 are also capable of exhibiting excellent fluid handling and skin dryness benefits, i.e, large volumes of fluid deposited on wearer contacting surface of the web are rapidly transferred to the non-wearer contacting surface of the web and the underlying absorbent substrate by virtue of the relatively large cross-section of capillary networks 1012, while capillary driven skin drying benefits are provided via the small scale capillary networks 1011 present in the non-debossed land areas which normally contact the wearer's skin in use. In addition, it is believed that the upward projections associated with the tiny capillary networks 1011 act as a network of baffles during gush flow situations, i.e., large quantities of liquid deposited on the wearer contacting surface are caused to flow in many different directions before reaching an edge of the absorbent structure, thereby increasing the probability that the liquid will enter one or more of the macroscopic cross-section capillary networks 1012 before reaching an edge of the absorbent structure.

The macroscopically expanded, three-dimensional, apertured plastic web 1010 shown in FIGS. 6 and 7 was formed from 1 mil thick polyethylene which was first apertured on a fine scale mesh screen comprised of wire monofilaments having a diameter of about 3.7 mils and a mesh count of 120 filaments by 120 filaments per inch. The finely apertured web was thereafter reverse wrapped onto a macroscopic forming structure exhibiting an overall thickness of 16 mils and a regularly spaced pattern of substantially round apertures, each measuring approximately 26 mils at its point of maximum width, said apertures being spaced approximately 67 mils from one another, center-to-center distance. The web was formed using a two-phase forming process of the type generally disclosed in FIG. 1 of the aforementioned, commonly assigned U.S. patent application of John J. Curro, James C. Baird, Donald L. Gerth, George M. Vernon and E. Kelly Linman entitled MULTI-PHASE PROCESS FOR DEBOSSING AND PERFORATING A POLYMERIC WEB TO COINCIDE WITH THE IMAGE OF ONE OR MORE THREE-DIMENSIONAL FORMING STRUCTURES, Ser. No. 740,145, said application being concurrently filed herewith and incorporated herein by reference. The process was carried out by applying a pressure of 1000 psig and a water flow rate of 10 gallons per minute per inch of web width at the first high pressure liquid nozzle and a pressure of 500 psig and a water flow rate of 8 gallons per minute per inch of web width at the second high pressure liquid nozzle. Both vacuum chambers were maintained at 2 inches of mercury. The resultant web 1010 exhibited an overall caliper of approximately 20 mils, as measured under no load, and a soft and pleasing tactile impression, particularly in those non-debossed areas coinciding with the land areas of the forming structure.

The specific process conditions under which macroscopically expanded, three-dimensional web 1010 was produced and the apparatus utilized are more fully described in connection with Example I, which is hereinafter set forth:

EXAMPLE I

The macroscopically expanded, three-dimensional, apertured polymeric web 1010 shown in FIGS. 6 and 7 was made in step-wise fashion, generally following the two stages of the process disclosed in FIG. 1 of the aforementioned U.S. patent application of John J. Curro, James C. Baird, Donald L. Gerth, George M. Vernon and E. Kelly Linman entitled MULTI-PHASE PROCESS FOR DEBOSSING AND PERFORATING A POLYMERIC WEB TO COINCIDE WITH THE IMAGE OF ONE OR MORE THREE-DIMENSIONAL FORMING STRUCTURES, Ser. No. 740,145, said application being concurrently filed herewith and incorporated herein by reference. The input web was low density polyethylene, 1 mil thick (Consolidated Thermoplastics, #24765, Harrington, Del. 19952). This web was fed onto the fine wire forming structure at a speed of 500 feet per minute and subjected to the high pressure water jet. The water temperature was 165° F., the water pressure about 1000 psig, and the water flow about 10 gallons per minute per cross-machine direction inch of web width. The first forming structure was a woven wire 120×120 mesh screen, having 0.0037 inch wires. (Cambridge Wire Cloth Co., Cambridge, Md. 21613.) This first stage produced a web containing a multiplicity of small capillary networks 1011, approximately 0.004 inches in diameter, at a density of 120 such capillary networks per linear inch in both directions. This finely apertured web was then wound onto a take-up roll. The second stage was carried out by taping a 6 inch by 12 inch portion of the aforementioned finely apertured web onto a different forming structure. This forming structure contained apertures of approximately 0.026 inch in diameter spaced 0.067 inches center-to-center on a 60° array. The finely apertured web was reverse wrapped (small capillary networks oriented toward the second high pressure liquid nozzle) on the latter forming structure and subjected to a second high pressure water jet at a web speed of approximately 500 feet per minute. The water temperature was 155° F., the water pressure was about 500 psig and the water flow was approximately 8 gallons per minute per cross-machine direction inch of web width. The resultant macroscopically expanded, three-dimensional, apertured web shown in greatly enlarged form in FIGS. 6 and 7 contained small elliptically shaped capillary networks 1011 measuring approximately 0.004 inches across their major axis and macroscopic cross-section, elliptically shaped macroscopic cross-section capillary networks 1012 measuring approximately 0.022 inches across their major axis. The overall no load caliper of the expanded web was approximately 0.015 inches.

From the foregoing description it is apparent that webs of the present invention provide the gush flow handling and resistance to rewet characteristics achievable using macroscopically expanded, three-dimensional plastic webs of the type disclosed in the aforementioned commonly assigned patents to Thompson and to Radel et al. However, unlike prior art webs, webs of the present invention can also provide predetermined capillary suction pressures previously obtainable, it at all, only on a random basis in fibrous webs. Furthermore, unlike prior art fibrous webs which exhibit a random pore structure due to their methods of manufacture, the gush handling and capillary suction characteristics of polymeric webs of the present invention are precisely controllable on a repetitive basis and may be adjusted upwardly or downwardly, as desired, by careful selection of the size, shape and quantity of macroscopic cross-section and fine scale capillary networks. In addition, webs of the present invention can be made to exhibit a highly desirable visual and tactile impression. It will be further appreciated by those skilled in the art that the present invention may be practiced to particularly great advantage in situations where very specific fluid transfer characteristics are desired by the user, and these particular characteristics do not happen to coincide with the characteristics inherent in conventional prior art webs.

While the present invention has been described in the context of a topsheet for a disposable absorbent bandage, it is, of course, recognized that the present invention may also be practiced to advantage in many other environments where controlled fluid transmission and/or isolation is desired. It will be obvious to those skilled in the art that various changes and modifications can be made without departing from the spirit and scope of the invention, and it is intended to cover in the appended claims all such modifications that are within the scope of this invention.

What is claimed is:

1. A macroscopically expanded, three-dimensional fluid-handling polymeric web having first and second surfaces located in substantially parallel planes which are remote from one another, said web including a multiplicity of fluid-handling capillary networks of macroscopic cross-section for rapidly transmitting fluids which are dynamically deposited on said first surface of said web to said second surface of said web using the dynamic and gravitational head of the fluid as a primary driving force, each of said macroscopic cross-section capillary networks originating as an aperture in said first surface of said web and having a continuously interconnected sidewall extending in the direction of said second surface of said web, said continuously interconnected sidewall terminating to form at least one aperture in said second surface of said web, whereby the bulk of said dynamically deposited fluid is transmitted from said first surface to said second surface of said web by said macroscopic cross-section capillary networks, said first surface of said web in which said macroscopic cross-section capillary networks originate further including a multiplicity of fluid-handling capillary networks which are substantially smaller in cross-section than said macroscopic cross-section fluid-handling capillary networks, said smaller fluid-handling capillary networks exhibiting a degree of capillary suction sufficient to transmit static fluid contained on the surface of objects which contact said first surface of said web generally in the direction of said second surface of said web by capillary attraction.

2. The web of claim 1, wherein said smaller cross-section capillary networks originate as an aperture in said first surface of said web and have a continuously interconnected sidewall extending in a direction opposite said second surface of said web, said continuously interconnected sidewall terminating to form at least one aperture in a third surface remote from the first and second surfaces of said web.

3. The web of claim 2, wherein said apertures in said third surface of said web form volcano-like cusps which exhibit a soft and silky tactile impression.

4. The web of claim 1, wherein the perpendicular distance between the first and second surfaces of said web is at least about 7 mils.

5. The web of claim 1, wherein the perpendicular distance between said first and said second surfaces of said web is at least about 15 mils.

6. The web of claim 1, wherein the cross-sectional shape of each of said smaller capillary networks is defined by a major axis which coincides with the maximum cross-sectional dimension of said network and a minor axis which coincides with the minimum cross-sectional dimension of said network, as measured perpendicular to said major axis of said network, and wherein the maximum dimension of said minor axis is less than about 20 mils.

7. The web of claim 1, wherein the cross-sectional shape of each of said smaller capillary networks is defined by a major axis which coincides with the maximum cross-sectional dimension of said network and a minor axis which coincides with the minimum cross-sectional dimension of said network, as measured perpendicular to said major axis of said network, and wherein the maximum dimension of said minor axis is less than about 10 mils.

8. The web of claim 1, wherein each of said macroscopic cross-section capillary networks is defined by a major axis which coincides with the maximum cross-sectional dimension of said network and a minor axis which coincides with the minimum cross-sectional dimension of said network, as measured perpendicular to said major axis of said network, and wherein the minimum dimension of said minor axis is at least about 20 mils.

9. The web of claim 1, wherein said macroscopic cross-section capillary networks are irregular in shape.

10. The web of claim 1, wherein said smaller capillary networks are of irregular cross-section.

11. The web of claim 1, wherein said macroscopic cross-section capillary networks are of dissimilar cross-sectional area.

12. The web of claim 1, wherein said smaller capillary networks are of dissimilar cross-sectional area.

13. A macroscopically expanded, three-dimensional, resilient, fluid-handling polymeric web having first and second surfaces located in substantially parallel planes which are separated from one another by a distance of at least about 7 mils, said web including a multiplicity of fluid-handling capillary networks of macroscopic cross-section for rapidly transmitting fluids which are dynamically deposited on said first surface of said web to said second surface of said web using the dynamic and gravitational head of the fluid as a primary driving force, each of said macroscopic cross-section capillary networks having a minor axis dimension of at least about 20 mils and originating as an aperture in said first surface of said web and having a continuously interconnected sidewall extending in the direction of said second surface of said web, said continuously interconnected sidewall terminating to form at least one aperture in said second surface of said web, whereby the bulk of said dynamically deposited fluid is transmitted from said first surface to said second surface of said web by said macroscopic cross-section capillary networks, said first surface of said web in which said macroscopic cross-section capillary networks originate further including a multiplicity of fluid-handling capillary networks which are substantially smaller in cross-section than said macroscopic cross-section fluid-handling capillary networks, said smaller fluid-handling capillary networks exhibiting a degree of capillary suction sufficient to transmit static fluid contained on the surface of objects which contact said first surface of said web generally in the direction of said second surface of said web by capillary attraction.

14. The web of claim 13, wherein said smaller cross-section capillary networks originate as an aperture in said first surface of said web and have a continuously interconnected sidewall extending in a direction opposite said second surface of said web, said continuously interconnected sidewall terminating to form at least one aperture in a third surface remote from the first and second surfaces of said web.

15. The web of claim 13, wherein said apertures in said third surface of said web form volcano-like cusps which exhibit a soft and silky tactile impression.

16. The web of claim 13, wherein the cross-sectional shape of each of said smaller capillary networks is defined by a major axis which coincides with the maximum cross-sectional dimension of said network and a minor axis which coincides with the minimum cross-sectional dimension of said network, as measured perpendicular to said major axis of said network, and wherein the maximum dimension of said minor axis is less than about 20 mils.

17. The web of claim 13, wherein the cross-sectional shape of each of said smaller capillary networks is defined by a major axis which coincides with the maximum cross-sectional dimension of said network and a minor axis which coincides with the minimum cross-sectional dimension of said network, as measured perpendicular to said major axis of said network, and wherein the maximum dimension of said minor axis is less than about 10 mils.

18. The web of claim 13, wherein each of said macroscopic cross-section capillary networks exhibits a cylindrical shape.

19. The web of claim 13, wherein said macroscopic cross-section capillary networks are irregular in shape.

20. The web of claim 13, wherein said smaller capillary networks are of irregular cross-section.

21. The web of claim 13, wherein said macroscopic cross-section capillary networks are of dissimilar cross-sectional area.

22. The web of claim 13, wherein said smaller capillary networks are of dissimilar cross-sectional area.

23. An absorbent bandage comprising an absorbent element having a wearer contacting topsheet secured in superposed relation thereto, said topsheet comprising a macroscopically expanded, three-dimensional fluid-handling polymeric web having a first wearer contacting surface and second absorbent element contacting surface located in substantially parallel planes which are remote from one another, said web including a multiplicity of fluid-handling capillary networks of macroscopic cross-section for rapidly transmitting fluids which are dynamically deposited on said first surface of said web to said second surface of said web using the dynamic and gravitational head of the fluid as a primary driving force, each of said macroscopic cross-section capillary networks originating as an aperture in said first surface of said web and having a continuously interconnected sidewall extending in the direction of said second surface of said web, said continuously interconnected sidewall terminating to form at least one aperture in said second surface of said web, whereby the bulk of said dynamically deposited fluid is transmitted from said first surface to said second surface of said web by said macroscopic cross-section capillary networks, said first surface of said web in which said macroscopic cross-section capillary networks originate further including a multiplicity of fluid-handling capillary networks which are substantially smaller in cross-section than said macroscopic cross-section fluid-handling capillary networks, said smaller fluid-handling capillary networks exhibiting a degree of capillary suction sufficient to transmit static fluid contained on the surface of objects which contact said first surface of said web generally in the direction of said second surface of said web by capillary attraction.

24. The absorbent bandage of claim 23, wherein said absorbent elements exhibits a greater degree of capillary suction than the smaller capillary networks, whereby said static fluid is drawn through said smaller capillary networks and into said absorbent element.

25. The absorbent bandage of claim 23, including a moisture-impervious backsheet secured adjacent the surface of said absorbent element opposite said topsheet.

26. A macroscopically expanded, three-dimensional fluid-handling polymeric web having first and second surfaces located in substantially parallel planes which are remote from one another, said web including a multiplicity of dual purpose fluid-handling capillary networks, said dual purpose capillary networks having a macroscopic cross-section portion for rapidly transmitting fluids which are dynamically deposited on said first surface of said web to said second surface of said web using the dynamic and gravitational head of the fluid as a primary driving force, each of said dual purpose capillary networks originating as an aperture in said first surface of said web and having a continuously interconnected sidewall extending in the direction of said second surface of said web, said continuously interconnected sidewall terminating to form at least one aperture in said second surface of said web, whereby the bulk of said dynamically deposited fluid is transmitted from said first surface to said second surface of said web by said macroscopic cross-section portion of said dual purpose capillary networks, the perimeter of each of said dual purpose capillary networks also including at least one fluid-handling capillary network portion of substantially smaller cross-section than said macroscopic cross-section portion, said smaller fluid-handling capillary network portion exhibiting a degree of capillary suction sufficient to transmit static fluid contained on the surface of objects which contact said first surface of said web generally in the direction of said second surface of said web by capillary attraction.

27. The web of claim 26, wherein said dual purpose capillary networks exhibit a star shaped cross-section.

28. The web of claim 26, wherein said dual purpose capillary networks exhibit a snowflake shaped cross-section.

29. The web of claim 26, wherein said dual purpose capillary networks exhibit a dogbone shaped cross-section.

30. The web of claim 27, wherein the points of said star comprise said smaller fluid-handling capillary network portion.

* * * * *